United States Patent
Frey

(10) Patent No.: US 7,550,000 B2
(45) Date of Patent: Jun. 23, 2009

(54) RESTRICTOR REGULATED AIR FLOW BLANKET, SYSTEM UTILIZING SUCH BLANKET AND METHOD THEREFOR

(75) Inventor: William E. Frey, Kingston, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 600 days.

(21) Appl. No.: 11/138,447

(22) Filed: May 27, 2005

(65) Prior Publication Data
US 2006/0271134 A1    Nov. 30, 2006

(51) Int. Cl.
*A61F 7/00* (2006.01)
(52) U.S. Cl. .......................... 607/104; 607/107; 607/108
(58) Field of Classification Search ................. 607/104, 607/107, 108–112
See application file for complete search history.

(56) References Cited

U.S. PATENT DOCUMENTS

| | | | |
|---|---|---|---|
| 5,300,098 A | 4/1994 | Philipot | |
| 5,785,723 A * | 7/1998 | Beran et al. | 607/104 |
| 5,839,133 A | 11/1998 | Dickerhoff | |
| 6,440,157 B1 | 8/2002 | Shigezawa et al. | |
| 2003/0036786 A1* | 2/2003 | Duren et al. | 607/96 |
| 2004/0153132 A1 | 8/2004 | Cobb et al. | |

* cited by examiner

*Primary Examiner*—Roy D Gibson
(74) *Attorney, Agent, or Firm*—Louis Woo

(57) ABSTRACT

To reduce the amount of air input to a patient warming blanket, when the blanket is of a size that does not require the full amount of air output from a convective warmer for optimal pressurization, a regulator is provided to the inlet of the blanket to restrict the amount of air input to the blanket, thereby reducing the airflow rate to one that is appropriate for the optimal inflation or pressurization of the warming blanket. Respective regulators that allow different amounts of air under pressure to pass therethrough may be correspondingly fitted to blankets of different sizes and/or dimensions. Each regulator fitted to the inlet of the blanket may be configured in the form of an adapter with multiple orifices for passage of air, or a filter made of an air permeable material having a preselected porosity.

20 Claims, 6 Drawing Sheets

US 7,550,000 B2

RESTRICTOR REGULATED AIR FLOW BLANKET, SYSTEM UTILIZING SUCH BLANKET AND METHOD THEREFOR

FIELD OF THE INVENTION

The present invention relates to warming blankets and particularly to a warming blanket that has fitted thereto a restrictor for controlling the flow rate of air input to the blanket. The present invention also relates to a system in which blankets of various dimensions each are equipped with a corresponding restrictor so that each of the blankets is adapted to be optimally inflated by the same air convective warmer, irrespective of the different dimensions of the blankets.

BACKGROUND OF THE INVENTION

To hypothermically warm a patient, a convective warmer to which a warming blanket is connected is used. There are various convective warming blanket types that exist in the market today. The various blankets have different dimensions. In most instances, these blankets are each inflated by a convective warmer, such as the Level 1 Equator™ warmer, that operates at only one speed. Thus, the same amount of air is output from the warmer to inflate the different blankets irrespective of the size of the blanket that is connected to the warmer.

Insofar as the different blankets have different sizes, as for example from a full adult size blanket to a neonate blanket, and those blankets have different exhaust capabilities, the existing convective warmers such as for example the aforenoted Level 1 Equator™ system use differently sized outlet hoses adapted to mate with the differently sized blankets. For example, for a regular adult size blanket, a regular outlet hose is used. However, if the convective warmer were to be used to provide heated air to a pediatric warming blanket, which has a smaller dimension than a regular adult blanket, a special hose has to be fitted to the convective warmer so that a portion of the heated air is either blocked or bypassed from the blanket. This is due to the fact that a full size adult blanket requires a higher air flow rate and thus a greater volume of air in order to be inflated with the proper pressure, with the heated air coming out of, or exhausting from, the various holes or slits of the blanket to warm the patient. On the other hand, for a smaller warming blanket such as for example a pediatric blanket, the same amount of air input to the blanket, if possible, will over inflate the blanket. As a result, to inflate the pediatric blanket, a different hose has to be configured for the outlet of the convective warmer to bypass a portion of the output air so that the pediatric blanket could be properly inflated, and the proper output of heated air provided to warm the child patient covered by the blanket.

In co-pending applications entitled "System for Providing Actuated Optimal Inflation to Multiple Temperature Regulated Blankets and Method Therefor", application Ser. No. 11/061,882 and "System for Providing Optimal Inflation to Multiple Temperature Regulated Blankets and Method Therefor", application Ser. No. 11/061,871, both filed on Feb. 18, 2005 and assigned to the same assignee as the instant application, systems for inflating patient warming blankets of different dimensions at respective optimal flow rates are disclosed. The '882 system requires the actuation of at least one switch for activating the system. In the '871 system, a sensor provided at the outlet of the system provides a feedback for controlling the flow rate of air to inflate the blanket. For such feedback system, an expensive sensor, and an accompanying feedback circuit are required. The respective disclosures of the '882 and the '871 applications are incorporated herein by reference.

In co-pending application entitled "System for Automatically Inflating Temperature Regulated Blankets and a Blanket for Coupling to the System", application Ser. No. 11/080,481 filed on Mar. 16, 2005 and assigned to the same assignee as the instant invention, there is disclosed a blanket, and system therefor, that has a code positioned on the body of the blanket to provide an indication to a convection warmer of the flow rate of air required to optimally inflate the blanket, when the blanket is connected to the convective warmer. The disclosure of the '481 application is incorporated by reference herein.

SUMMARY OF THE PRESENT INVENTION

The present invention discloses a patient warming blanket that passively and automatically controls the amount of air that is allowed to be fed into the blanket at a given time so that the desired flow rate of air for optimally inflating the blanket to provide clinically desired warming therapy for the patient is achieved.

The warming blanket of the present invention in particular is fitted with a regulator or restrictor configured to restrict the air flow rate from the convective warmer to provide optimum pressurization for the blanket, when the blanket is connected to the convection warmer. By controlling the air flow into a blanket of a given size mechanically by means of the regulator fitted to the inlet of the blanket, a fixed flow rate predetermined to optimally inflate the blanket of that given size is allowed to pass the restrictor, thereby providing optimal pressurization and air flow for the particular sized blanket.

Patient warming blankets of different sizes from neonate to full adult size may each be fitted with a corresponding restrictor preconfigured to allow a flow rate of air that would optimally inflate the particular blanket. The respective blankets may each be connected to the same air convection warmer that outputs air at its outlet at a fixed air flow rate.

For the instant invention blanket, a regulator or restrictor is provided at the inlet of the blanket to regulate the amount of heated air input to the blanket at an airflow rate that has been predetermined to provide optimum pressurization for the blanket, or optimally inflate the blanket, so that the desirable clinical results are achieved for the patient covered by the blanket. The air regulator may be in the form of a cup with multiple orifices or holes formed thereat, so that air exhausts from the restrictor would have an air flow rate that, albeit possibly different from the flow rate of the heated air from the convective warmer, would nonetheless optimally inflate the particular blanket.

The blanket of the instant invention includes an inflatable body having a first side and a second side, with one of the sides being in contact with the subject patient covered by the blanket. The blanket has an inlet for mating to an outlet of a convective warmer so that heated air from the convective warmer is input to the inflatable body. A regulator means is provided at the inlet of the blanket to regulate the amount of heated air input to the inflatable body at a predetermined optimal flow rate for the body so that effective therapy for the patient covered by the blanket could be effected by the heated air escaping from the openings provided on the one side of the blanket that is in contact with the patient.

A second embodiment of the instant invention relates to an apparatus that comprises a convective warmer having an outlet, a heater for heating the air in a plenum in the warmer, and an air blower or impeller for directing the heated air to the outlet at a preset flow rate. Connected to the convective warmer is a warming blanket having an inflatable body, an inlet mated to the outlet of the warmer for establishing a flow path to the warmer, and a regulator provided at the inlet to allow the heated air from the warmer to be input to the body at a flow rate preselected for the blanket to inflate the blanket.

The instant invention also relates to a system in which a convective warmer has a heater for heating air in the plenum of the warmer and an air blower or impeller for directing the heated air to an outlet to which warming blankets of different sizes may be connected. The heated air from the warmer is output at a first flow rate. A plurality of blankets each are adaptable to be connected to the convective warmer. To connect a blanket to the warmer, the inlet of the blanket is mated to the outlet of the warmer. For each of the plurality of warming blankets that may be connected to the convective warmer, a regulator is provided at its inlet to control the amount of heated air to be input to the blanket at a desired flow rate for that blanket. The desired flow rate for each of the blankets may be different from the flow rate of the air output from the convective warmer. That notwithstanding, with a customized regulator for each blanket, once connected to the warmer, each blanket is optimally inflated.

The present invention also relates to a method for optimally inflating a patient warming blanket that has an inflatable body and an inlet to allow heated air from a warmer to be input to the body. The steps include determining a desired flow rate of air to be input to the blanket that would optimally inflate the blanket, effecting an air regulator that controls the amount of air that could pass therethrough at the determined desired flow rate, and providing the regulator at the inlet of the blanket so as to maintain the amount of heated air input to the blanket at the desired flow rate.

The instant invention therefore provides a passive way to control the air input to a blanket that is designed specifically for each of the blankets irrespective of the dimension or size of the blanket. To achieve this end, each of the blankets is fitted with a pressure control unit such as an air regulator or restrictor that is designed to allow air to pass therethrough at a fixed flow rate predetermined to provide optimum pressurization for the blanket. Blankets of various sizes each may then be optimally pressurized using the same source of pressurized air.

BRIEF DESCRIPTION OF THE FIGURES

The present invention will become apparent and the invention will be best understood with reference to the following description of embodiments of the present invention taken in conjunction with the accompany drawings, wherein.

DETAILED DESCRIPTION OF THE INVENTION

Figure 1:
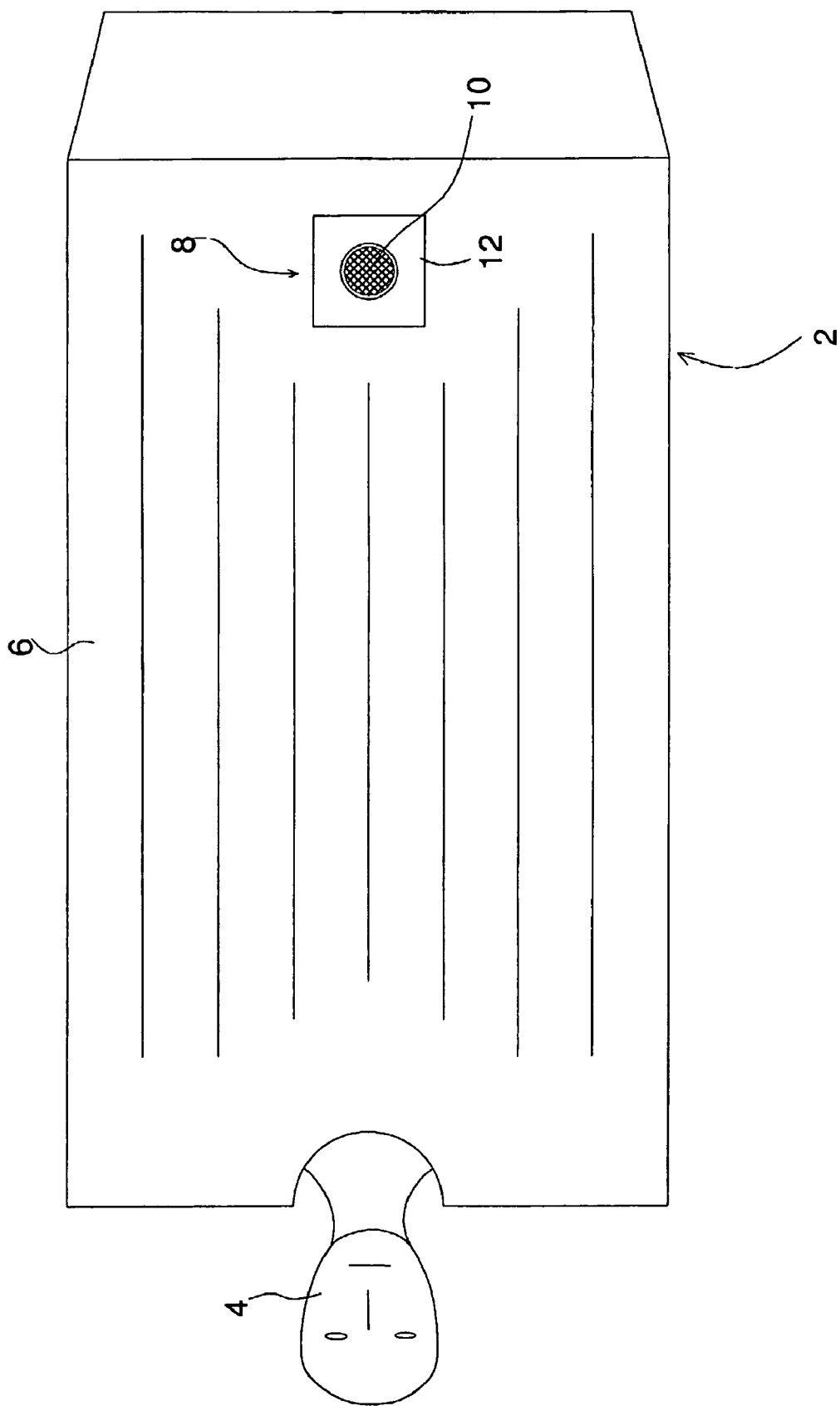
FIG. 1 shows a subject patient covered by an exemplar patient warming blanket adapted to be fitted with the air flow restriction mechanism of the instant invention.

FIG. 1 is a plan view of a patient warming blanket that may be based on the blankets currently being sold by the assignee of the instant invention. For example, blanket 2 may be an adult full size blanket sold by the assignee under manufacturer No. SW-2001. Alternatively, blanket 2 may be a smaller size blanket, or may even be a neonate blanket to be used for infants and newborns.

As shown, a subject patient 4 is covered by blanket 2. As is well known, warming blanket 2 is made up of an inflatable body 6 that has two sides, the side facing the reader and a side that is in contact with subject 4. The side that is in contact with the subject has a number of openings or slits, not shown, that allow heated air in the blanket to exhaust to thereby warm or provide clinical therapy to the subject.

As shown, blanket 2 has an inlet 8 that has an opening 10 through which a fluid such as air heated by an air convection warmer is input to the blanket to inflate body 6. Inlet 8 is adapted to mate with an outlet hose, such as 14 shown in FIGS. 2-4, of a convective warmer.

Figure 2:
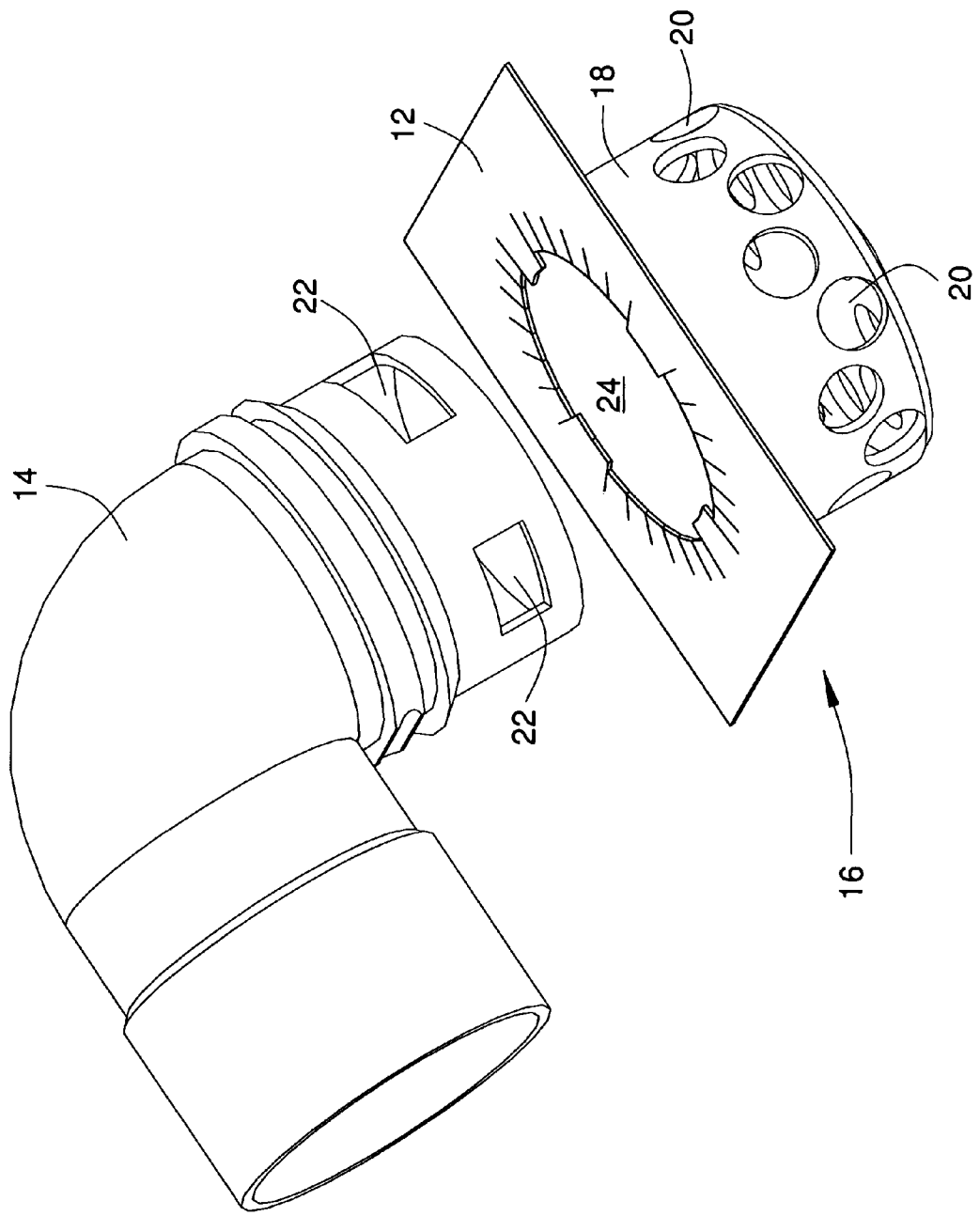
FIG. 2 is a perspective view of an air flow restrictor or regulator and an air hose from the convective warmer matable therewith.
Figure 3:
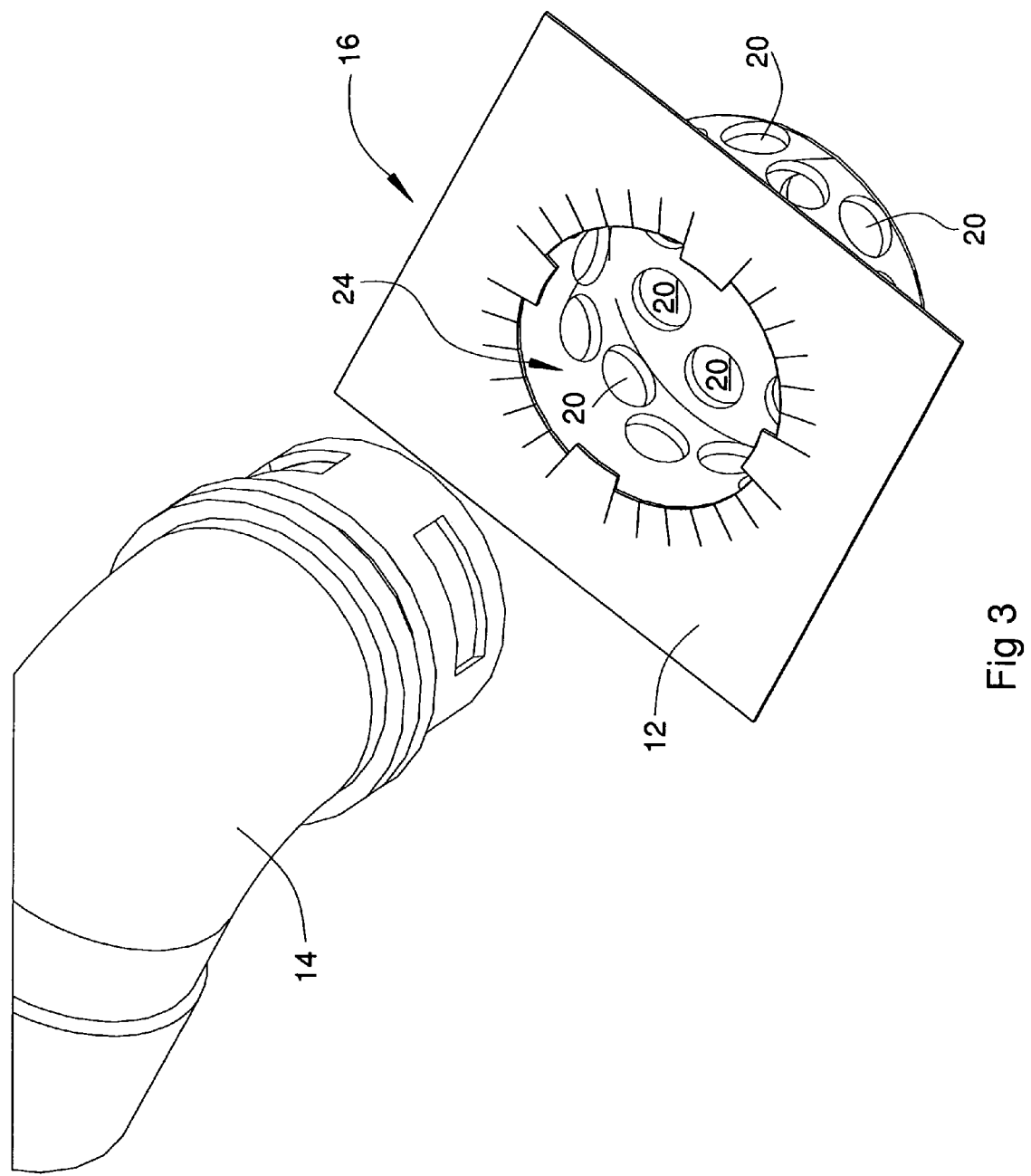
FIG. 3 is another view of the air flow restrictor at the inlet of a blanket and the outlet hose of an air convective warmer.
Figure 4:
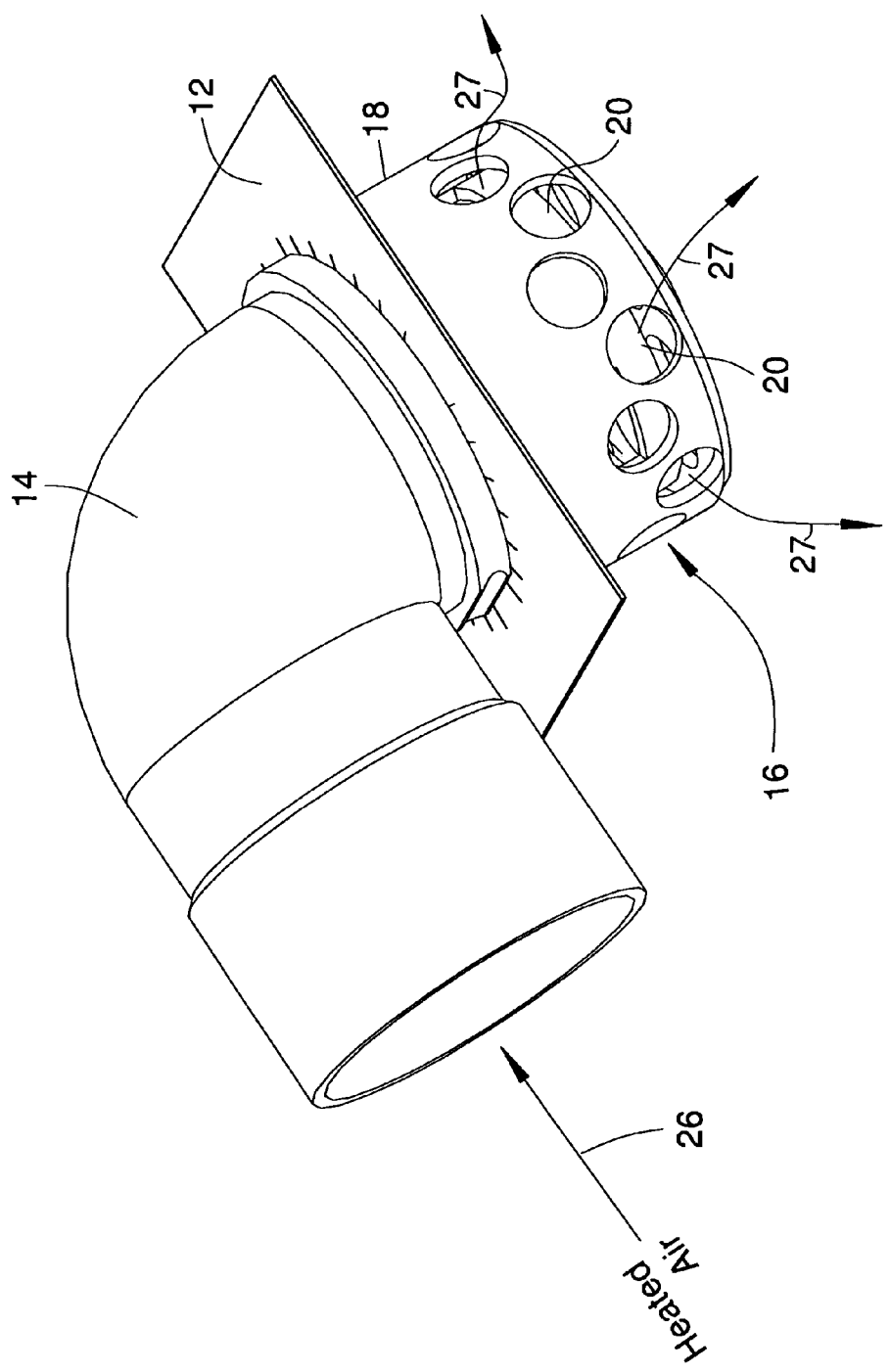
FIG. 4 shows the outlet hose of the convective warmer being connected or mated to the flow restrictor or regulator shown in FIGS. 2 and 3.

With reference to FIGS. 2-4, for the instant invention blanket, a means for regulating the amount of heated air input to the body is provided at inlet 8. Such means may be a restrictor or regulator mechanism as shown in FIGS. 2-4. The top of regulator 16, which may be a stiffener 12 made of plastic or cardboard, enables the regulator to be bonded, or fixedly connected, to the warming blanket at its outlet.

The exemplar air flow regulator or restrictor shown in FIGS. 2-4 includes the top stiffener and a cup shaped extension 18 that is adapted to fit to inlet 8 of blanket 2. As shown, a number of orifices or holes 20 are formed at extension 18 so that a portion of the air output from the convective warmer and fed to its outlet, as exemplified by outlet hose 14, would pass through the multiple orifices and be input to the body of the warming blanket to which regulator 16 is fitted. There are a number of apertures or openings 22 provided circumferentially at the distal end of outlet hose 14 that mates to central opening 24 of regulator 16 to facilitate the passage of air from outlet hose 14 to the blanket.

Regulator 16 is configured to allow the heated air from outlet 14 of the convective warmer into the body of the blanket at a desired flow rate preselected for that particular blanket. The desired flow rate is dependent on the dimension or size of the blanket.

In a conventional air convection warmer, the heated air, under pressure, is directed to the outlet of the warmer at a flow rate speed of approximately 2100 ft/min. Such flow rate has been calculated to optimally inflate a full size adult blanket, and was designed not to cause excessive backpressure build-up that may damage the convective warmer. Yet to optimally pressurize a blanket that is not full size, for example a blanket for a child that has a dimension smaller than a full size adult blanket, an air flow rate of only approximately 1700 ft/min is desired. By providing customized air flow regulator 16 as shown to its inlet, the amount of air under pressure fed to such smaller size blanket is passively controlled and maintained at the desirable air flow rate of approximately 1700 ft/min, as regulator 16 restricts the amount of air that flows freely into the blanket.

The determination of the optimal air flow for a warming blanket of a given dimension may be readily achieved by conventional calculations or empirical studies, so that different regulators with correspondingly different numbers of orifices 20 may be provided for blankets of different sizes. As is readily apparent, for a neonate blanket, the regulator fitted to that blanket would have a smaller number of orifices 20 formed at extension 18, as compared to a regulator that is to be used with an adult size blanket. Thus, even though the air output from the air convective warmer may be at a substantially constant air flow rate of 2100 ft/min, by adapting respective appropriate regulators to the different sized blankets, each of the blankets may be optimally inflated. For instance, the air for inflating a child blanket may be reduced to a desired flow rate of approximately 1700 ft/min, while the air for inflating a neonate blanket may be reduced yet further to a desired flow rate of approximately 1300 ft/min.

The passage of air from the warmer to a blanket is best shown in FIG. 4. There, heated air output by the air convection warmer is shown to be routed in the direction indicated by directional arrow 26 into outlet hose 14, and from there to regulator 16, and finally exiting from the exemplar multiple orifices 20 of regulator 16 per directional arrows 27 to inflate the blanket. As long as the blanket is optimally inflated or maintained at its desired pressure, the heated air exhausted from the slits of the blanket that overlay the patient would provide the desired heat therapy to the patient.

Figure 5:
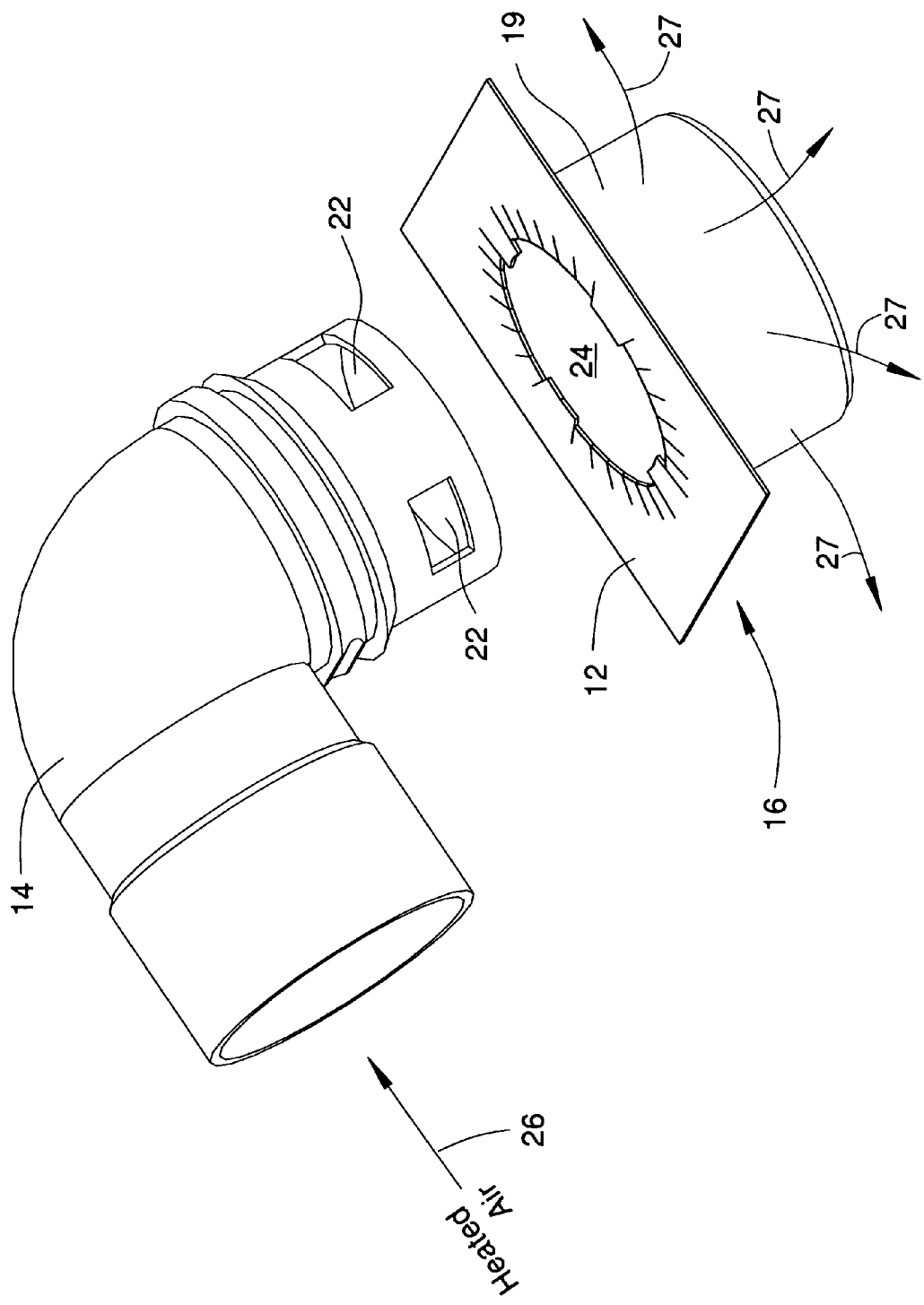
FIG. 5 shows the outlet hose of the convective warmer relative to another embodiment of a flow restrictor or regulator.

Instead of the regulator 16 as shown in FIGS. 2-4, an air regulator adapted to be used with the inventive blankets of the instant invention may be made of a porous material having a porosity that allows air to be exhausted into the blanket at the desired flow rate. Such non-hole filter 19 is shown in FIG. 5 where directional arrows 27 illustrate the outflow of air when outlet 14 is mated to opening 24 of regulator 19. The air flow regulator of the instant invention may therefore be a filter made up of an air permeable material such as filter paper, membrane or foam with respective predetermined porosities for warming blankets of different dimensions.

Further, instead of a hard material such as plastic or cardboard, regulator 16 as shown in the figures may be made of a flexible material, which allows for the folding of the blanket, and also the possibility of making the blanket thinner for packaging. Moreover, even though orifices or holes 20 of the same size and shape are illustrated for the air regulator exemplarily shown in the figures, it should be appreciated that the multiple orifices may in fact have different sizes and shapes, as long as the amount of air allowed to pass through it is predetermined to be the desired amount or flow rate for the particular blanket to which the regulator is adoptedly fitted. The number of orifices 20 for the regulators may also vary for blankets of different sizes.

Figure 6:
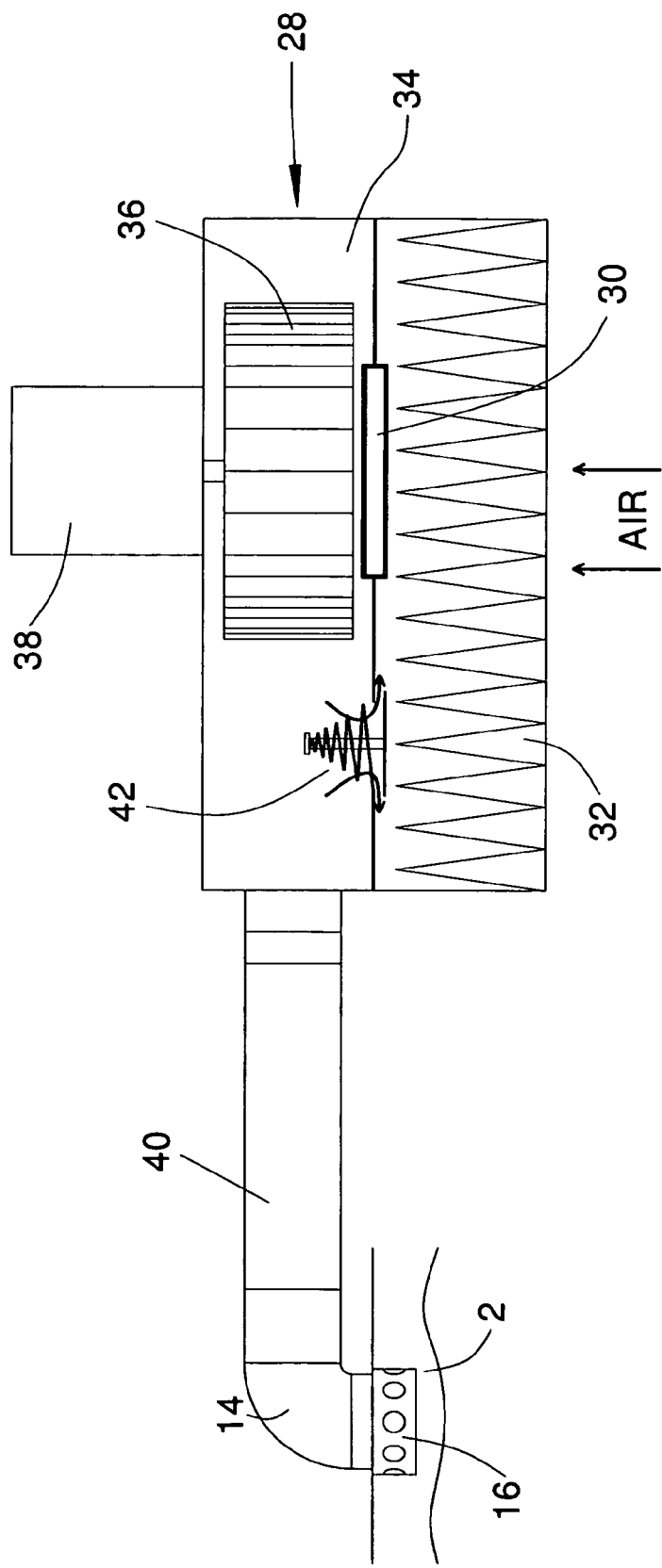
FIG. 6 is a schematic diagram showing a system whereby a blanket fitted with an air restrictor is connected to the outlet hose of a convective warmer so that the heated air from the warmer is fed to the blanket.

FIG. 6 shows the overall system of the instant invention. As shown, the system includes an air convective warmer 28 connected to blanket 2 by means of a hose 40, outlet 14 and regulator 16. Thus connected, a fluid communication path is provided between blanket 2 and convective warmer 28, so that the heated air from warmer 28 is directed to blanket 2 for inflation or pressurization thereof.

Air convective warmer 28 is shown to include a filter 32 for filtering the input air that enters into a plenum 34 whereat the air is heated by a heater 30. The heated air is blown by an air blower or impeller 36, which is driven by a motor 38, to outlet 14, which is part of hose 40, for inflating blanket 2. With the proper regulator 16 for restricting or regulating the amount of air input thereto, blanket 2 is optimally inflated so as to be maintained at the proper pressure.

Due to the fact that only a portion of pressurized air is allowed to pass through regulator 16, backpressure would build-up in convective warmer 28. To ensure that this backpressure does not cause any damage to convection warmer 28, a bypass valve 42 may be provided to exhaust the excess air to the air intake. An exemplar by-pass valve may commence bypassing of excess air at 0.07 psi. Although a poppet type valve is shown in the FIG. 6 warmer, other types of low pressure bypass valve arrangement may also be used.

It should be appreciated that the present invention is subject to many variations, modifications and changes in detail. Accordingly, the matter described throughout this specification and shown in the accompany drawings should be interpreted as illustrative only and not in a limiting sense.

The invention claimed is:

1. A blanket for covering a subject, comprising:
  an inflatable body having a first side and a second side, one of the sides being in contact with the subject;
  an inlet at said body for receiving an outlet of a convective warmer so that heated air from the convective warmer is input to the body;
  openings provided at the one side contacting the subject to allow the heated air inside the blanket to escape to provide therapy for the subject; and
  air regulator means fitted to said inlet to regulate the amount of heated air input to said body at a predetermined optimal flow rate for said body to provide effective therapy for the subject when said inlet receives said outlet of said warmer.

2. Blanket of claim 1, wherein said air regulator means provided at said inlet comprises an air regulator having multiple orifices the number of which selected to allow said predetermined optimal flow rate of heated air to be input to said body.

3. Blanket of claim 2, wherein said regulator comprises a flexible filter.

4. Blanket of claim 1, wherein said air regulator means provided at said inlet comprises a filter made from a porous material having a porosity that allows said predetermined optimal flow rate of heated air to pass into said body.

5. Apparatus, comprising:
  a convective warmer having an outlet, a heater for heating air in a plenum of said warmer, and an air blower for directing the heated air to said outlet at a preset flow rate; and
  a warming blanket having an inflatable body, an inlet instable to said outlet to establish a fluid path to said warmer, and an air regulator fitted to said in let for allowing the heated air from said warmer to be input to said body at a flow rate preselected for said blanket to inflate said blanket when said outlet is mated to said inlet.

6. Apparatus of claim 5, wherein said regulator comprises an adapter fitted to said inlet, said adapter having multiple orifices the number of which selected to allow said preselected flow rate of heated air to be input to said body.

7. Apparatus of claim 6, wherein said regulator comprises a flexible filter.

8. Apparatus of claim 5, wherein said regulator is made from a porous material having a porosity designed to allow said preselected flow rate of heated air to pass into said body.

9. Apparatus of claim 5, wherein said warmer comprises a backpressure valve to allow air in excess of the amount to be optimally input to said blanket to escape from said warmer to thereby prevent backpressure from being built up in said warmer.

10. Apparatus of claim 5, wherein the amount of heated air directed to said outlet of said warmer has an air speed of approximately 2100 ft/mm, and wherein said regulator appropriately reduces the air speed of the heated air input to said blanket to optimally inflate said blanket.

11. A method of optimally inflating a patient warming blanket having an inflatable body and an inlet to allow heated air from a warmer to be input to the body, comprising the steps of:
  determining a desired flow rate of air to be input to said blanket that would optimally inflate said blanket;
  effecting an air regulator to control the amount of air to pass therethrough at said desired flow rate; and
  providing said regulator fitted to said inlet of said blanket;
  wherein when an outlet of said warmer is connected to said inlet, said regulator at said inlet controls the amount of heated air input to said body of said blanket at said desired flow rate.

12. Method of claim 11, further comprising the step of:
  providing multiple orifices in said regulator wherethrough the heated air passes.

13. Method of claim 11, wherein said effecting step further comprises the step of:
  making said regulator from an air permeable material having a porosity that allows said desired flow rate of air to pass therethrough.

14. System, comprising:
  a convective warmer having a heater for heating air in a plenum of said warmer and an air blower for directing the heated air to an outlet to which respective ones of a plurality of warming blankets of different dimensions are matable to said warmer, the heated air being directed to the outlet at a first flow rate;
  at least one of said plurality of blankets adapted to fluidly connect to said warmer at any one time, each of said plurality of blankets having an inflatable body of a given dimension and an inlet adapted to mate with said outlet of said warmer to establish a fluid communication path whereby heated air from said warmer is input to said each blanket for inflating said each blanket; and
  a regulator provided at the inlet fitted to the inlet of said one blanket for controlling the amount of heated air to be input to said one blanket at a desired flow rate adapted to optimally inflate said one blanket when said outlet of said warmer is mated to said inlet.

15. System of claim 14, wherein each of said plurality of blankets is fitted with a given regulator at its inlet for selectively controlling the amount of heated air to be input to said each blanket at a flow rate corresponding to the dimension of the body of said each blanket.

16. System of claim 14, wherein the regulator for each of said plurality of blankets comprises an adapter filled to the inlet of said each blanket, said adapter having multiple orifices the number of which selected to allow the heated air to be input to the body of said each blanket at said desired flow rate for said each blanket.

17. System of claim 14, wherein the regulator of each of said plurality of blankets is made from a porous material having a porosity that allows the heated air to be input to the body of said each blanket at the desired flow rate for said each blanket.

18. System of claim 14, wherein said warmer comprises a backpressure valve to allow air in excess of the amount to be input to any of the respective ones of said plurality of blankets connected to its outlet to escape from said warmer to thereby prevent excess air pressure in said warmer.

19. System of claim 14, wherein said first flow rate is approximately 2100 ft/mm, and wherein the regulator of said each blanket may reduce the flow rate of air input to said each blanket to one that is appropriate for optimally inflating said each blanket.

20. System of claim 14, wherein each of said plurality of blankets is fitted with a given regulator at its inlet for selectively controlling the amount of heated air to be input to said each blanket at a flow rate based on the amount of air needed to maintain a proper pressurize for said each blanket.

* * * * *